United States Patent [19]
Snook

[11] Patent Number: 5,735,283
[45] Date of Patent: Apr. 7, 1998

[54] SURGICAL KERATOMETER SYSTEM FOR MEASURING SURFACE TOPOGRAPHY OF A CORNEA DURING SURGERY

[76] Inventor: Richard Kieth Snook, 8050 N. Tackroom La., Tucson, Ariz. 85741

[21] Appl. No.: 727,920
[22] Filed: Oct. 9, 1996
[51] Int. Cl.⁶ ............................................. A61B 3/107
[52] U.S. Cl. .................. 128/664; 128/665; 128/653.1; 128/745; 351/211; 351/212
[58] Field of Search ................... 128/653.1, 664, 128/665, 745; 351/205, 212, 211, 221

[56] References Cited

U.S. PATENT DOCUMENTS

| Re. 27,475 | 9/1972 | Volk | 351/39 |
|---|---|---|---|
| 3,248,162 | 4/1966 | Knoll | 351/6 |
| 3,264,932 | 8/1966 | Hendricks | 88/24 |
| 3,542,458 | 11/1970 | Volk | 351/39 |
| 3,598,478 | 8/1971 | Townsley | 351/6 |
| 3,797,921 | 3/1974 | Kilmer et al. | 351/7 |
| 4,439,023 | 3/1984 | Iba et al. | 351/206 |
| 4,440,447 | 4/1984 | Schacher | 351/212 |
| 4,523,820 | 6/1985 | Kaakinen | 351/206 |
| 4,523,821 | 6/1985 | Lang et al. | 351/214 |
| 4,978,213 | 12/1990 | El Hage | 351/212 |
| 4,984,883 | 1/1991 | Winocur | 351/212 |
| 5,106,183 | 4/1992 | Yoder | 351/212 |
| 5,131,739 | 7/1992 | Katsuragi | 351/212 |
| 5,159,361 | 10/1992 | Cambier et al. | 351/212 |
| 5,206,672 | 4/1993 | Rowe | 351/212 |
| 5,220,360 | 6/1993 | Verdooner | 351/212 |
| 5,302,979 | 4/1994 | Maeda et al. | 351/212 |
| 5,309,186 | 5/1994 | Mizuno | 351/212 |
| 5,325,135 | 6/1994 | Nakamura et al. | 351/212 |
| 5,349,398 | 9/1994 | Koester | 351/212 |
| 5,384,608 | 1/1995 | Gersten | 351/212 |
| 5,398,084 | 3/1995 | Jian | 351/212 |
| 5,406,342 | 4/1995 | Jongsman | 351/212 |
| 5,416,538 | 5/1995 | Yamada | 351/212 |
| 5,418,582 | 5/1995 | van Saarloos | 351/212 |
| 5,440,393 | 8/1995 | Wenz | 356/376 |
| 5,463,430 | 10/1995 | Isogai et al. | 351/208 |
| 5,473,392 | 12/1995 | Klopotek | 351/205 |
| 5,475,452 | 12/1995 | Kuhn et al. | 351/212 |
| 5,500,697 | 3/1996 | Fujieda | 351/212 |
| 5,512,965 | 4/1996 | Snook | 351/205 |
| 5,512,966 | 4/1996 | Snook | 351/205 |
| 5,519,485 | 5/1996 | Ohtani et al. | 356/2 |
| 5,521,657 | 5/1996 | Klopotek | 351/212 |
| 5,526,073 | 6/1996 | Mattioli | 351/212 |
| 5,548,355 | 8/1996 | Iki | 351/212 |
| 5,585,872 | 12/1996 | Kohayakawa | 351/212 |
| 5,592,246 | 1/1997 | Kuhn et al. | 351/212 |
| 5,640,962 | 6/1997 | Jean et al. | 128/664 |
| 5,668,623 | 9/1997 | Sakurai et al. | 351/212 |

Primary Examiner—Marvin M. Lateef
Assistant Examiner—Eleni Mantis Mercader
Attorney, Agent, or Firm—Benman & Collins

[57] ABSTRACT

This invention relates to certain improvements in the art of keratometry and, more particularly, to the use of television techniques to determine the shape of the corneal surface of an eye in essentially real-time. Paired television images of diffuse reflections from the cornea are produced by projecting an infra-red illuminated pattern onto the cornea. These diffuse reflections are compared by triangulation to define the corneal contour. The resultant data are processed by a conventional microcomputer to derive surface contour for display, the shape data so generated in a form for instant use. Compensation for image brightness at each location is provided by altering camera video amplifier gain on a pixel by pixel basis, thereby linearizing the response in photometric units. The linearization reduces the complexity of the digital signal processing required for producing a contour map of the cornea. The present invention specifically relates to devices that are used with surgical microscopes.

18 Claims, 5 Drawing Sheets

*Fig. 5a* Raster Detail

*Fig. 5*

63+ microseconds

Fig. 8 ian is a figure shown here, which is a schematic diagram of a surgical keratometer system.

SURGICAL KERATOMETER SYSTEM FOR MEASURING SURFACE TOPOGRAPHY OF A CORNEA DURING SURGERY

BACKGROUND OF THE INVENTION

1. Field of the Invention

The present invention relates generally to photo-keratometry, and more particularly, to improvements in the art of photo-keratometry wherein a diffuse reflection of a projected, illuminated surface or other target is formed on the cornea. This diffuse reflection is analyzed to determine the surface contour of the eye. The present invention specifically relates to devices that are used with surgical microscopes.

2. Description of Related Art

The instrument that is in most common use for central-optical-zone shape measurement, in conjunction with the surgical microscope, is the Terry keratometer. Several companies offer similar devices, from outright copies to apparatus redesigned using a similar principle of operation. These devices require the user to operate one or more controls. These controls are employed to bring Mire images that are reflected from two perpendicular axes on the surface of the eye, simultaneously into focus and alignment. Alternatively, the user selects a comparison reticle for size assessment in each axis. Disadvantageously, these controls are difficult to operate and provide poor repeatability.

However, all prior art surgical keratometers require the surgeon to manipulate knobs, levers, or the like and, thus, raise the problem of sterility control. In general, either the surgeon must change gloves after operating the device, or, in some cases, the knobs are covered by sterile plastic devices. Even though covers are applied, there is the chance that the user will contact non-sterile surfaces when this technique is employed.

Prior art devices also require that the tear film on the eye surface be intact since reflection from this film is central to the measurement technique. The tear film is typically not constant in thickness during surgery and, in some cases, may not be present at all. This variable thickness or outright absence of the tear film prevents meaningful measurements of the corneal shape during surgical procedures on the anterior portion of the eye.

Representative of video keratometers for microscope use is the KM-1000 manufactured by Nidek Inc. of Japan. A placido (bulls-eye target) is illuminated by an infra-red source, and a video image of the infra-red reflex is examined by conventional video analysis means.

Prior art systems, however, are costly, complex, and slow, and modifications, if required, are difficult to implement. Thus, it follows that another system for characterizing the eye must be employed in order to produce a functional instrument within the speed and cost constraints required for commercial viability. Additionally, a practical system must be suitable for operation by unsophisticated users. These above-listed factors, as well as other criteria, require a departure from the traditional techniques for keratometry and image analysis.

In recent times, keratometric attachments to the ophthalmic surgical microscope have been more commonly used. In spite of the number of systems in use today, universal satisfaction with the results of these systems have not been obtained.

The basic premise in the design of the optical portion of each of the prior art instruments is similar, and the problems associated with their use can be grouped into instrument design and operational error segments.

Inherent in the prior art systems are several assumptions that bear upon the accuracy of the measurements.

1. The I.O.P. (intra-ocular pressure) is assumed to be in the normal range for the eye being examined.

2. The curvature in all meridians is assumed to be essentially symmetrical around the visual axis.

3. The microscope is assumed to be critically focused in the reflex image plane; that is, the surgeon is not accommodating.

4. The optical axis of the microscope is assumed to be perpendicular to and coincident with the visual axis of the eye being examined.

5. The microscope does not change focal plane with changes of magnification.

6. The measurement of the anterior surface curvature in dioptric terms is assumed to be an accurate measure of the focusing power of the eye.

The limitations of these assumptions are presented in sequence below:

1. Although the I.O.P. is assumed to be in the normal range in conventional systems, in reality, the I.O.P. is not reflected by either the infusion or the aspiration pressures because of the hydro-dynamics of the tubing, eye, and varying lumen cross-sections involved in the infusion/aspiration systems.

2. Despite the conventional assumption that the curvature in all meridians is symmetrical around the visual axis, the anterior surface of the cornea is neither perfectly spherical nor is the visual axis coincident with the optical axis in the normal human eye. (The anterior surface of the normal cornea is not quite a spherical form, but more nearly an evolute ellipsoid.)

3. Even though in conventional systems the microscope is assumed to be critically focused in the reflex image plane, more often than not, the focus is only approximate. Typically, the surgeon is compensating both by accommodation and by increasing the light level so that the iris of surgeon's eye is constricted, thereby providing an increased depth of focus.

4. As described above, the optical axis of the microscope is conventionally assumed to be perpendicular to and coincident with the visual axis of the eye being examined. However, in practice, the microscope is seldom aligned perpendicular to the floor. Additionally, the X–Y position is seldom exactly centered on the optical axis of the eye, even if the eye being examined is properly fixated.

5. That conventional microscopes do not change focal planes with changes of magnification is unlikely. Even the most expensive microscopes exhibit some degree of focal shift with power change, particularly those with zoom power changers. To use the zoom microscope fitted with a keratometer of the prior art, either the system must compensate for this shift, or the measurement must be made at a selected magnification (typically, minimum power).

6. The conventional assumption that the measurement of the anterior surface curvature, in dioptric terms, is an accurate measure of the focusing power of the eye is also invalid. The primary focusing element of the eye is the tear film on the anterior surface of the cornea. However, no single surface measurement can define the focal characteristics of a multiple-element, optical system. Additionally, the conversion of local surface curvature into dioptric terms assumes an index of refraction that is not a true value but, rather, is a calibration constant derived by experiment. However, this "constant" value varies with different manufacturers of keratometers and ophthalmometers. (Several manufacturers of keratometers and ophthalmometers use slightly different values.) Thus, even though the measured value, as modified by the internal calibration constant, is supposed to represent the dioptric correction needed to achieve emmetropic correction, none of these provide a direct assessment of the corrective lens power required for the eye being measured.

Beyond these caveats is the assumption that any moving parts associated with the attachment may be manipulated by the surgeon without loss of sterility and that there is no possibility of particulates being released by the mechanism above the sterile field. It is further assumed that the displayed data are available in real-time and in a form and location that is easy to use.

None of the currently available surgical keratometers, however, are designed to overcome most of these above-mentioned problems. Additionally, the prior art systems exhibit a wide range of error and are inconvenient to operate.

Thus, there remains a need for an apparatus and method for measuring the surface of the eye during surgery that avoids most, if not all, the foregoing problems.

SUMMARY OF THE INVENTION

In accordance with the present invention, an instrument is provided for measuring surface topography of a cornea during surgery. The instrument comprises the following:

(a) an optical projector that projects a pattern onto the cornea, the pattern comprising a plurality of isolated points;

(b) a first camera and a second camera each comprising a camera lens and a detector array, the first camera, the second camera, and the projector directed toward a single point, the first camera and the second camera producing images of the plurality of isolated points projected on the cornea, the location of each of the isolated points on the cornea dependent upon the surface topography;

(c) a computer processor that employs triangulation calculations to determine the surface topography from the location of the isolated points on the cornea; and (d) a display for displaying the surface topography.

The method of the present invention, which is intended for measuring surface topography on a cornea during surgery, comprises the following steps:

(a) projecting a pattern onto the cornea using a projector, the pattern comprising a plurality of discrete points, the location of each of the discrete points on the cornea dependent upon the surface topography;

(b) directing a first camera, a second camera, and the projector toward a single point in space;

(c) placing the cornea at a position between the single point in space and the first camera, the second camera, and the projector;

(d) obtaining images of the discrete points projected on the cornea with the first camera and the second camera;

(e) employing triangulation calculations to determine the surface topography from the location of the discrete points on the cornea; and (f) displaying the surface topography.

The object of this invention is to provide an improvement in the art of photo-keratometry as employed in conjunction with surgical microscopes where the measurement of diffusely reflected image points projected on the cornea is analyzed, and the corneal curvature is derived. A second object is to provide the surface shape data to a surgeon in the operating room for use in controlling post-operative astigmatism. A further object of this invention is to construct a system that imposes only a low cost on the user and thereby makes the system competitive in the marketplace. An additional object is to include automatic derivation and display of corneal radii with the corresponding axis of measurement. Another object of the invention is to develop a "user friendly" system that is operable without any special training or skill and that produces quick and accurate readings of corneal data. A further object of this invention is to offer an improvement in the art of image analysis, as applied to keratometry and similar measurements, and to reduce the complexity of the computations (as well as apparatus) thereby permitting almost "real-time" analysis. Another object of this invention is the construction of a keratometer that may be used with a surgical microscope that does not require the user to manipulate knobs, levers, or other actuators with the attendant risk of contamination of the sterile field. An additional object of this invention is to provide variable surface shape resolution for use either in a conventional surgical keratometer or in a small area measuring device for analysis of laser ablation results before any significant edema has occurred.

DESCRIPTION OF THE PREFERRED EMBODIMENTS

Reference is now made in detail to a specific embodiment of the present invention, which illustrates the best mode presently contemplated by the inventor for practicing the invention. Alternative embodiments are also briefly described as applicable.

After a review of the historical and current instrument literature, several experiments were made that led to the present invention, which is directed to a method and apparatus for characterizing the shape of a human cornea during surgery.

In the present invention, a plurality of illuminated target points are projected onto the eye while paired television cameras, which are connected to a computer, are employed to analyze the corneal shape of the eye using stereo photogrammetric techniques. In particular, the formation of a series of points in the focal plane of a projector of conventional design produces diffuse reflections within the bulk of the corneal tissue. These points are viewed by paired television cameras mounted at known angles to the axis of projection. The television cameras produce stereo pairs of the images that are in temporal and spatial registration. The paired television images are used to define the topography of the corneal surface by a process of triangulation within the associated computer for display to the user while a surgical process is performed.

Figure 1:
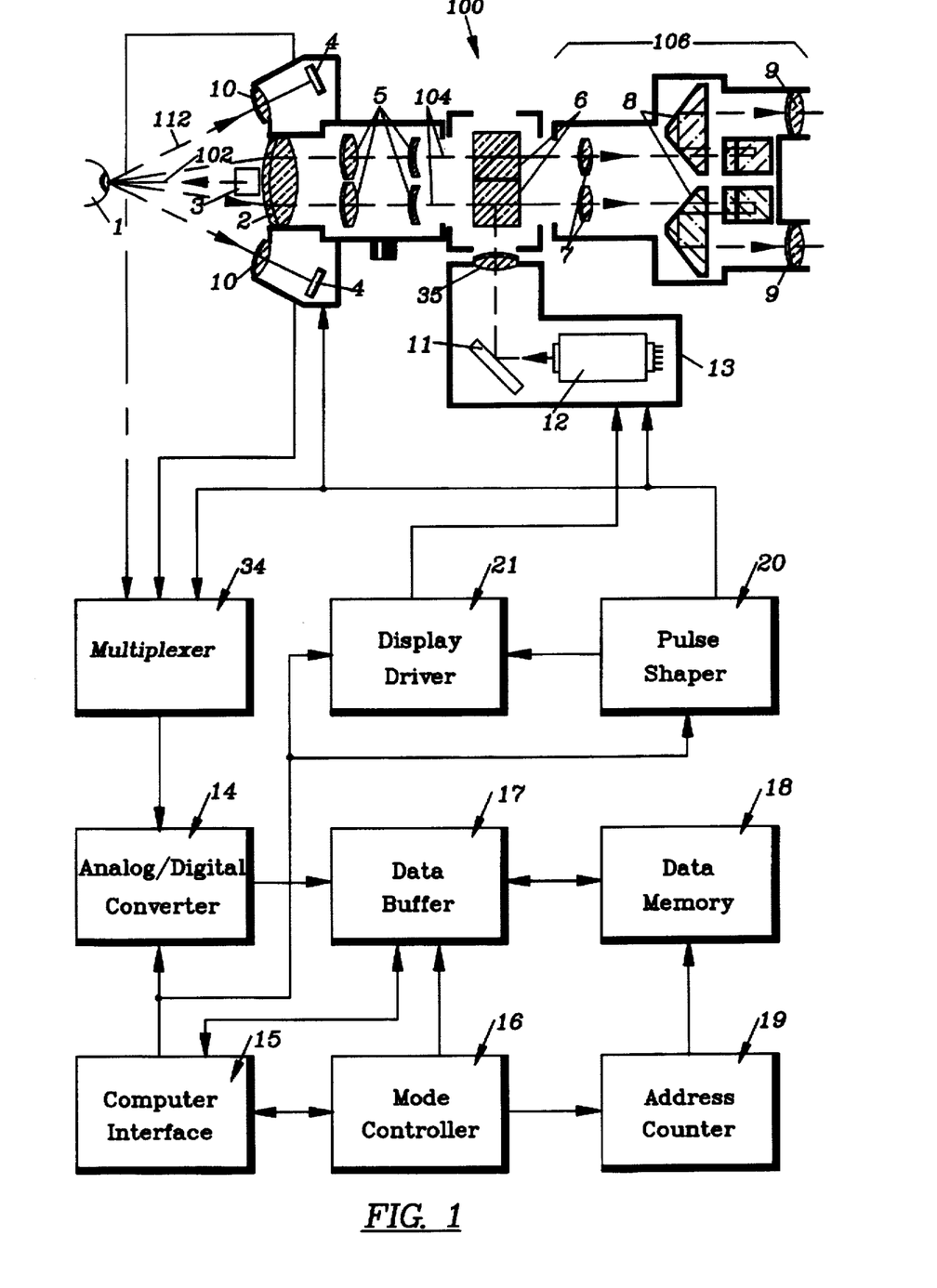
FIG. 1 is a cross-sectional view and accompanying block diagram depicting the system of the present invention.

FIG. 1 shows a schematic view and block diagram of the apparatus of the present invention. The apparatus of the present invention comprises a simple attachment for a surgical microscope 100. An eye 1 that is to be examined is placed at the focus of an objective lens 2 of the microscope 100. The projector system (not shown) is employed to illuminate a target matrix 3. An image of the target matrix 3 is thereby formed on the eye 1. Specifically, the illuminated target matrix 3 is reflected by the anterior surface of the cornea via a mirror located on the optical axis 102 of the objective lens 2 and centered between the paired optical axes 104 of the microscope 100. Tyndall images of the matrix projection are formed in the cornea and are imaged on charge coupled devices 4 by lenses 10 aligned and focused at the focal point of the microscope objective lens 2. The microscope 100 is equipped with a beamsplitter system 6 for providing access to the microscope image path. The image of the eye 1 is magnified or minified by the power changer 5 which produces an erect virtual image at optical infinity. The virtual image of the eye 1 is, in turn, magnified by the eyepiece assembly 106 that comprises an objective lens pair 7, an erector system pair 8, and paired eye lenses 9.

Attached to the microscope beamsplitter system 6 is a display assembly 13. The display assembly 13 is provided with an image display screen 12 and a suitable lens 35 to place the image of the screen into focus in one of the eye lenses 9 by the action of one of the beamsplitters 6.

To process the images formed in the cornea, a video signal from the charge coupled devices 4 is routed, via a time division multiplexer 34 of conventional design, to an analog to digital converter 14, a computer interface 15, and a data buffer 17. The computer interface 15 provides system timing and control for accepting and storing, the sequential paired pictures from the charge coupled devices 4. The data stream from the digitized pictures is stored in a data memory 18 under control of a computer (not shown) by the action of a mode controller 16 and an address counter 19. The computer interface 15 also provides video timing information via the pulse shaper 20 to all of the video devices to insure the capture of the desired pictorial sequence.

For displaying to the user, a fiducial figure is generated in the computer. This fiducial figure, with the calculated result of surface shape in graphical form, is displayed on a conventional video display 12. As described above, the display 12 is mounted in a housing 13 attached to one of the beamsplitter ports of the microscope 100. The beamsplitter assembly 6 is modified by the reversal of the associated beamsplitter prism 6 so that the display 12 is visible to the operator in the eye lens 9. The size of the attachment 13 may be reduced by beam folding with a prism or mirror 11 so that the bulk of the display housing is upright rather than extending to the side.

Lens 35 in the display assembly 13 provides the optical correction for viewing the image at optical infinity so that the view through the objective lens 2 and the display 12 are simultaneously in focus for viewing by the user. The display 12 may be provided with a foot-operated control so that the information is available only when called for to reduce the confusion that might result if the display were to be on continuously. The display driver 21 is controlled in temporal synchronism with the video signals through the action of a pulse shaper 20 under control of the computer via the computer interface 15.

In most, if not all, cases the exact surface contour of the eye 1 is of less interest to the clinician than the relative contour. For example, in a corneal transplant surgical case, the object is to adjust suture tension and location to arrive at a smooth, regular surface that has a similar contour in two perpendicular axes and is close to the pre-operative values (i.e., the induced distortion of the corneal surface is minimal). The errors of measurement are least at (or near) the center of the cornea, and the main image forming surface is encompassed by the same area. This fact permits the system of the present invention to be used in one configuration with a single target matrix projector attached to the microscope objective lens housing. In an alternative embodiment, the projection system employs a so-called "zoom lens" for determining the area of the corneal surface to be mapped so that the effective resolution may be enhanced by selecting a small area for analysis.

With a conventional ophthalmic microscope 100, an illuminated target 3, and associated television cameras 4, constructed according to the present invention, an image of the eye 1 is formed at optical infinity by the objective lens 2. This image is, in turn, imaged (at optical infinity) by the power changer system 5. The power changer system 5 may comprise a zoom system or Galilean telescopes so arranged as to magnify or minify the aerial image formed by the objective lens 2. This arrangement permits the use of fixed power, noninverting telescope assemblies 100 for observation. Additionally, the infinity focus of all elements enables the insertion of beamsplitters 6 into the image path without changing either magnification or plane of focus.

As described above, in the present invention, a portion of the image to one eye path is diverted by one of the beamsplitters 6 to provide a pictorial representation of the sphericity (or lack thereof) to the user, without requiring his or her eyes to be raised from the instrument. Additionally, the television cameras 4 are suitably mounted as to make a one-to-one image relationship between the two television pictures. Simultaneous capture of the paired images insures that there is no movement induced error in the spatial definitions derived. Thus, the pictorial content differs only by the geometric differences caused by the spaced relationship of the cameras 4 to the focal plane.

Figures 2, 3:
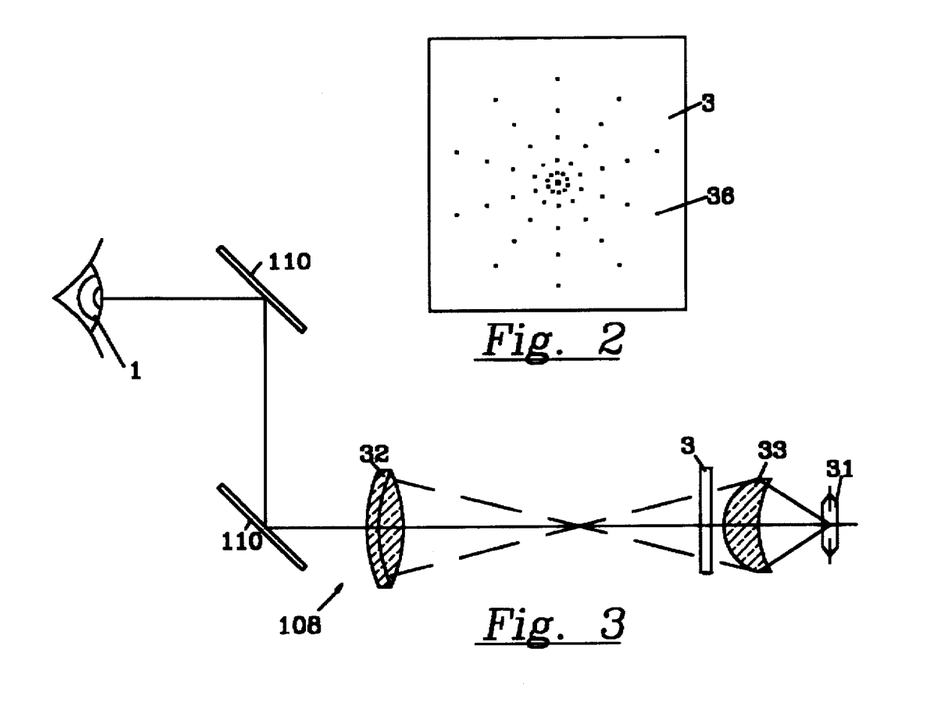
FIG. 2 is a schematic representation of the target matrix.
FIG. 3 is a cross-sectional view depicting the projector employed for producing a pattern image on the cornea.

Refer now to FIG. 2, which illustrates one version of the target matrix 3, an opaque, planar surface is provided with a plurality of transparent points 36 of small area that are arranged in a predetermined pattern. It will be appreciated that the pattern is not limited to the arrangement of transparent points 36 shown in FIG. 2, but may comprise any pattern of discrete points. The image of these points 36 formed by Rayleigh scattering within the bulk of the corneal tissue provides the data points that are used for defining corneal surface geometry in three dimensions.

To form an image of the target matrix 3 onto the eye 1, a projector system is employed. FIG. 3 shows a conventional projector system 108, which is mounted beneath the microscope 100. The projection path is folded by a pair of mirrors 110, one of which is located midway between the eyelines (or paired optical axes) 104 that run through the objective lens 2. This arrangement places the projection path on the centerline (or optical axis 102) of the microscope optical system 100. The object to be illuminated, target matrix 3, is an opaque plate with a matrix of small apertures, i.e., transparent points 36. The image of these point sources 36 is formed at the corneal surface. As shown in FIG. 3, the projector system 108 includes a light source 31, a condenser lens 33, and a projector lens 32. It will be appreciated that a small numerical aperture for the projection lens 32 assures adequate depth of focus so that the spots defined by diffuse reflection of the imaged points are sharply defined over the depth of the anterior chamber and corneal thickness.

As described above, the projector system 110 enables the set of illuminated points 36 in the object plane of the projector to be projected by the projection lens 32 onto the surface of the eye 1. The projection of these points 36 are viewed by the paired television cameras 4 mounted at known angles to the axis of projection (centerline 102). Accordingly, the television cameras 4 produce stereo pairs of the diffuse reflections within the bulk of the corneal tissue. These paired television images are used to define the corneal surface topography by a process of triangulation.

An essential feature of the apparatus of the present invention is that the optical axes (centerline 102) of the projector 108, and the optical axes 112 of the cameras 4 converge at a single point in three space. The optical axes 112 of the cameras 4 are defined by the ray that goes through the principal points of the camera lens 10. Similarly, the optical axes 102 of the projector 108 is defined by the ray that goes through the principal points of the projection lens 32.

If the beam from the projector 108 had not been intercepted by the cornea, it would have reached a plane defined by the intersection of these three optical axes (i.e., centerline 102 and the two optical axes 112) at known points. It will be appreciated that a reference plane can be made perpendicular to the optical axis 102 of the microscope objective lens 2 at the point of intersection which is at (or near) the normal focal point of the objective lens 2. This reference plane is behind the corneal surface.

Tyndall images of the illuminated points 36 in the object plane of the projector 108 are then produced at locations, in X and Y terms, that are a direct function of the sagittal depth of the cornea at each of the several image points so illuminated. The displacement of any given image point from the locus of intersection with the reference plane is, in turn, directly related to the sagittal depth at that particular image point. The pair of images is viewed by the paired television cameras 4 to define, in X and Y terms, the location of the points so illuminated.

Clearly, the surface geometry can be produced by a single camera 4 since all of the geometric data are available for such a definition. However, the present invention makes use of dual, stereo image pairs to increase the accuracy of measurement by (1) comparison of the simply derived X, Y, Z data from each image as well as (2) direct stereoptic reconstruction of the surface. This multiple reconstruction system provides an accuracy check as well as a means for eliminating spurious reflections from the corneal surface by objects or lights which might be present in the images.

The images from the paired cameras are converted into digital form by a sampling system commonly called a frame grabber. The stored digital images are compared in the associated computer, first by sequential subtraction to extract the target data from the background clutter and then left to right geometric comparison are made to determine the location in three space of the reflecting surface.

In an alternative embodiment, the television cameras 4 are so structured as to provide a digital representation of the video information as opposed to the common analog data output. The digital data take the form of byte wide serial transfer of brightness information.

As described above, a small numerical aperture for the projection lens 32 assures adequate depth of focus so that diffuse reflections of the imaged points are sharply defined over the depth of the anterior chamber and corneal thickness. To compensate for the small lens area, the illumination source 31 must be quite bright. In turn, the energy at the cornea from the light source 31 must not produce any measurable heating of the eye tissues. This task is accomplished by using an arc discharge type gas filled lamp having a flash duration that is short but bright. The pattern illumination is rendered in high contrast while the average power is kept quite low to achieve the desired goals. The lamp flash is controlled in time synchronism with the television camera vertical interval by the, computer type controller of the system. At intervals, preferably about one second, the tube (lamp) 31 is flashed and the image of the diffuse reflection of the projected spots is captured by an analog to digital conversion of the paired television images.

The general room illumination; surgical lights, and the like present a cluttered image that contains much extraneons information. To remove this clutter from the calculations, the present invention provides a spectral and temporal selection system that enables a reduction in the complexity of computation required for deriving the spatial data that represents the corneal surface shape.

The first method for reduction of this extraneous information is the limitation of the spectral content of the light from the target by insertion of suitable optical band pass filtration in the illumination path and similar filters in the television camera lens systems 10. The inherent sensitivity of silicon-based integrated circuit image sensors is the basis for the selection of the near infrared (IR) for the filters. With the use of the IR filters, the room ambient illumination is attenuated by a large amount while the target reflections are not.

The second method of reducing noise employed in the present invention involves synchronizing the time sequencing of the target illumination with the television camera timing. In this method described above, an image is received, digitized, and stored with the target illumination turned off. A second pair of images is subsequently acquired in similar manner with the target illumination provided. The first pair of images is numerically subtracted from the second pair so that any portions of the images that are substantially identical cancel, while the target image that exists only in the second exposures remains intact. The identification of the image points to be used for surface shape determination is then made by a simple numerical thresholding technique that removes the residual, noise induced, pictorial data that is not related to the desired target reflections from the paired viewing angles.

In the second method, which is directed to spectral selection, suitable IR optical bandpass filters are selected. The charge coupled device is inherently sensitive to near infra-red with a peak sensitivity at or near 750 nanometers. Dichroic filters with a narrow pass centered at this wavelength over the light source 31 and camera lenses 10 provide the removal of the background signal so that the data processing of the pictorial data is greatly simplified. The surgeon would not be aware of the measurements, which would be at about one frame per second or slower, since the infra-red light is not visible to the human eye. By pre-processing the video data stream in this fashion, the paired camera video streams can easily be processed at a rate adequate for almost real time data display without excessive cost per system.

In the second method described above for reducing noise employed in the present invention, the illumination of the target is alternately turned on and off in sequential image times. It follows that if two identical pictures were to be subtracted from each other, then the resultant image would be nil. In this case, however, there is a difference between the two images because of the action of the sequential illumination. This subtraction technique provides a less cluttered image from which the corneal shape can be derived by simpler computation, which is, therefore, faster and cheaper.

As described above, conventional television charge coupled devices 4 are mounted next to the microscope objective lens 2 for providing paired images of the reflection of the illuminated targets points 36 from the cornea. Subminiature television camera charge coupled devices 4 with adequate sensitivity and resolution are obtained quite cheaply and installed with suitable lenses 10 to provide coincident images from two known angles relative to the optical axis 102 of the microscope 100 and matrix projector 108. The paired charge coupled devices 4 generate the electronic images of the reflection to be analyzed.

The angles are established by the distance between the camera lens axes 112 and by the focal length of the objective lens 102 of the microscope 100. These factors are known, and so the angular position of the camera focal plane and lens optical axis 102 are established in manufacture. (As will be obvious to one skilled in the art, the angles can be made adjustable if interchangeable objective lenses 2 are to be employed).

In the apparatus of the present invention, the location of the principal points of the projector 108 and camera lenses 10 are accurately known by construction and test. Also, as described above, the optical axis (centerline 102) of the projector 108, and the optical axes 112 of the cameras 4 converge in a single point in three space. The axial distance and angle from the image points is then defined in the same manner as is disclosed in my previous patent, U.S. Pat. No. 5,512,965.

For each data point recovered from the first camera 4 coupled with the corresponding point from the second camera, calculations are made of the location on the corneal surface in three space coordinates. All corresponding reflections in each image pair are examined in a similar fashion. In this manner, the triangulation calculations establish a matrix of known surface points in three dimensions. A complete, or substantially complete, surface shape definition is constructed from the calculated location for many surface reflection points.

Figure 4:
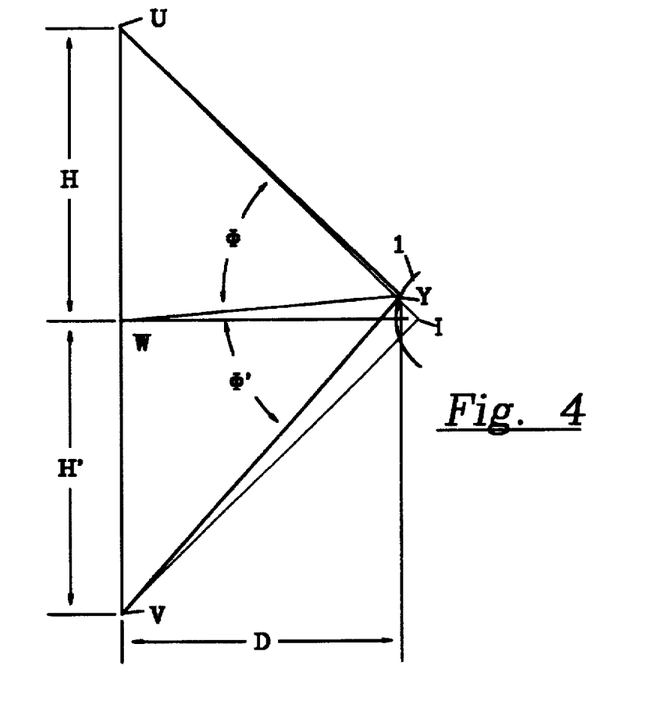
FIG. 4 is a schematic illustration depicting the optical geometry employed in the present invention.

Referring now to FIG. 4, which illustrates the geometry related to the triangulation method employed in the present invention. FIG. 4 shows the eye 1 and a point Y which corresponds to an image point formed on the eye. The front principal points of the paired camera lenses 10 are located at points U and V with their respective optical axes 112 defined by lines UI and VI. Similarly, the line WI corresponds to the optical axis 102 of the projector 108. The distance to the corneal surface of the eye 1 is roughly established by the operator who positions the microscope 100 to focus on the surface. The front principal point of the projector lens 32 is located at a point W with the distances H and H' established by construction of the system. As shown in FIG. 4, the two reference triangles, WIU and WIV, are coplanar. However, a discrete point 36 projected onto the cornea may lie in some plane above or below the plane defined by the two reference triangles.

The corneal surface is then defined by three effectively independent sets of calculations. The measuring rays from any given reflection are defined by triangles UYW and VYW. For any single projector image point Y on the cornea, angles $\Phi$ (UYW) and $\Phi'$ (VYW) can be established. Solution of the axial distance from Y to the system baseline UWV is by conventional trigonometry. Each triangle yields a solution for the distance with the composite solution producing a considerable accuracy enhancement over a single triangle solution of the prior art.

The present invention offers numerous advantages over the prior art, in particular, the technique described by Hjalmar Gullstrand in the last century. The most significant problem with the Gullstrand technique is that the central point is not measured; rather, the central point from which the surface must be defined is calculated from tangent slopes. The underlying assumption is that the central portion of the cornea is spherical and symmetrical. In fact, the central portion of the cornea is neither spherical nor symmetrical in the present invention, two surface constructions are made by triangulation, and these are combined by a second triangulation for removing the inherent errors of the prior art systems. The trigonometric derivation from the stereo pair data base is of better overall quality than the tangent slope derived models of the prior art measurement.

The prior art systems also must assume that the baseline distance from the objective lens 2 of the microscope 100 to the corneal surface is known and constant. In contrast, the present invention does not require this erroneous assumption as the triangulation data provide for recalculating the baseline distance.

In some cases, using the prior art technique the data reduction process requires several iterations to remove the distance error induced when the surgeon is accommodating to compensate for the inexact focus of the instrument. In the present invention, the diffuse reflections (as viewed from the spaced apart television cameras 4) differs by an amount determined by (1) the spacing between the camera lenses 10 and (2) the spacing between the camera lenses and the location of each reflection on the cornea. Thus, the surface shape is definable in terms of the different images from the paired cameras that are viewing the same reflected target from different angles.

To fully understand this invention, some knowledge of television signals is required. A television image that seems to the viewer to be a single stable image is, in fact, a blank screen most of the time. By making use of the persistence of vision and other psycho-physiological phenomena, the human visual system is tricked into perceiving a whole picture.

The picture is drawn by a beam of electrons that strike a phosphor coating inside the faceplate or viewing surface of the cathode ray tube where the image is formed. The phosphor emits visible light in direct proportion to the number of electrons per unit time that strike it and the energy of the particles in the beam. The beam is formed by thermal emission and electrostatic acceleration in an "electron gun" within the neck of the tube that is behind the viewing surface and, thus, out of view. The beam is focused by an electrostatic lens within the gun assembly so that the screen phosphor area that is bombarded at any instant is quite small compared to the entire screen. The illuminated spot is on the order of a few thousandths of an inch in diameter. This area is the only area on the entire screen that emits light to any significant extent at any given instant.

Figure 5:
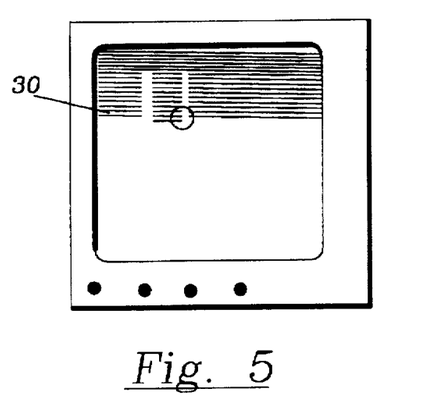
FIG. 5 is an illustration of image formation by a television "raster" on a monitor.
Figure 5A:
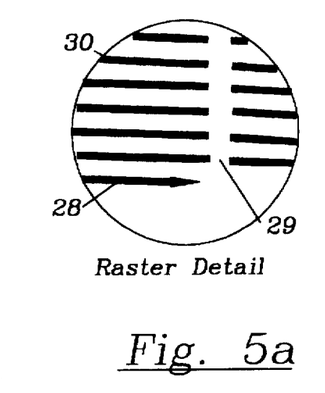
FIG. 5a is a magnified view of a small portion of the raster.

As illustrated in FIGS. 5 and 5a, which depict a television raster, the beam is swept over the surface of the faceplate in a regular pattern called a raster 30. Where the beam is incident on a particular area 28, that area is illuminated. In contrast, the areas 29 where the beam is not incident remain dark. This pattern was selected to permit a complete image to be formed without objectionable flicker and to limit the amount of radio spectrum required to transmit the information to the home.

The raster 30 is generated by deflecting the beam of electrons by an electromagnet assembly called a yoke. The beam is driven to the upper left corner (as viewed) at the start of each picture interval. The beam then sweeps across the faceplate from left to right to the other edge of the screen. At that time, the beam is turned off or "blanked" for a short time while the yoke signal is changed to start a new line at the left edge of the screen slightly below the first line. After this retrace interval, the beam is unblanked and the process is repeated. The actual image or frame is made in two interdigitated fields, each of which is, in theory, made up of 262.5 such lines (some of these lines do not result in any image formation but are outside the viewing area).

As the raster 30 is drawn, the intensity of the beam is modulated by the incoming signal so that the intensity of the light produced per unit area is a faithful reproduction of the transmitted scene. The image can be thought of as many discrete areas or picture elements (pixels) which are painted on the screen in time sequence. The area of a pixel, the smallest discrete pictorial element, is limited by the information transfer rate available. This rate was set for commercial broadcasting to fit in the amount of radio spectrum available. The NTSC (domestic broadcast standard) limits the rate of information to 4,500,000 elements per second.

The transmitted signal also contains synchronizing information required to keep the locus of the beam in step with the source at any time to insure undistorted restructuring of the sequential data into a picture. In particular, sync signals are included in the transmitted signals. The sync signals are included in the transmission as a part of the horizontal and vertical blanking intervals.

Figure 6:
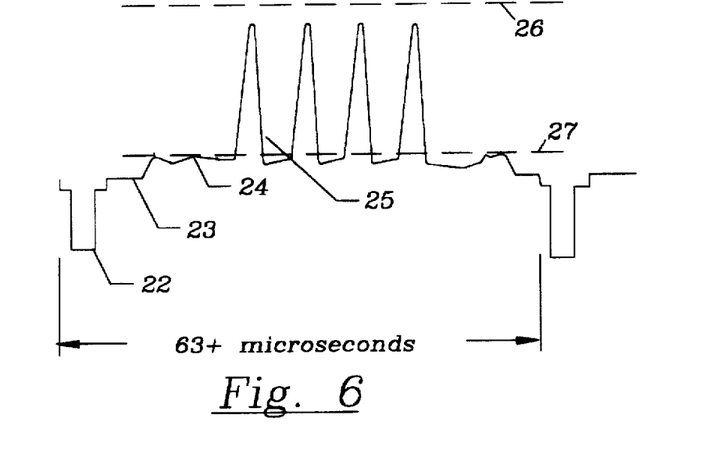
FIG. 6 on coordinates of voltage and time (in seconds), is a plot of the television signal waveform.

FIG. 6 shows the voltage waveform of a single raster line of video information. In particular, FIG. 6 illustrates the voltage amplitude or brightness versus time relationships. One horizontal line electrical signal is illustrated showing the timing and amplitude relationships of the signal. The electrical waveform illustrates a single line of the raster with alternating black and white areas. The horizontal sync pulse 22 is superimposed on a blanking signal 23 of such amplitude as to insure that the beam in the display is fully off during the retrace interval. Each successive raster line starts at the left edge, as viewed. The video signal, in this case at black level 24, is followed by four white areas 25. The definition of black and white are in terms of relative voltage magnitude above the "porch" or blanking level. There are two amplitudes that are pre-defined limits for the negative (black) and positive (white) voltages. The more positive clamp level is called the white clip level 26 and the video signal voltage is limited to this level when overbright objects or areas are photographed. The black clamp level 27 is adjustable based upon a sample of the image at a selected reference point. This is called keyed clamping.

The time between the horizontal sync signals in the NTSC standard is $1/15750$ second or 63.4 microseconds. The horizontal rate is 15,750 lines per second and the field and frame rates are 60 and 30 per second, respectively. From this, it follows that the pixel size can be defined in either size or time domain.

In conventional broadcast television the signal is limited to 4.5 Megahertz that yields a pixel rate of only 236 for the active or visible line of some 52.4 microseconds. The overscan of the display means that even fewer pixels make up the actual image viewed by the user. Even fewer elements are available for display in common cassette recording devices. These facts limit the inherent resolution of a television picture to a level much less than even a poor photograph, but the apparent motion and several other factors cause the perceived image to be acceptable when used as an entertainment medium.

For image analysis to perform the photogrammetric functions of keratometry, a higher resolution camera system is desirable. However, a high resolution can impose the problem of requiring more data to be analyzed to produce the corneal map.

As described above, the television cameras 4 may include charge coupled devices. A common, so-called charge coupled device solid-state camera uses an integrated circuit array of photoelectric cells arranged in rows and columns. A typical solid-state camera might have 525 or more elements (i.e., photo-diodes) in each line. The number of pixels per line will establish the pixel pitch or inherent resolution limit of a video camera which uses such a device in lieu of the more common vidicon or similar vacuum tube pickup element. It will be appreciated that the technique of the invention reduces the number of pixels required for analysis by employing a novel time sequence comparison method to permit the computer solution to be derived faster and with fewer steps and pixels.

Figure 7:
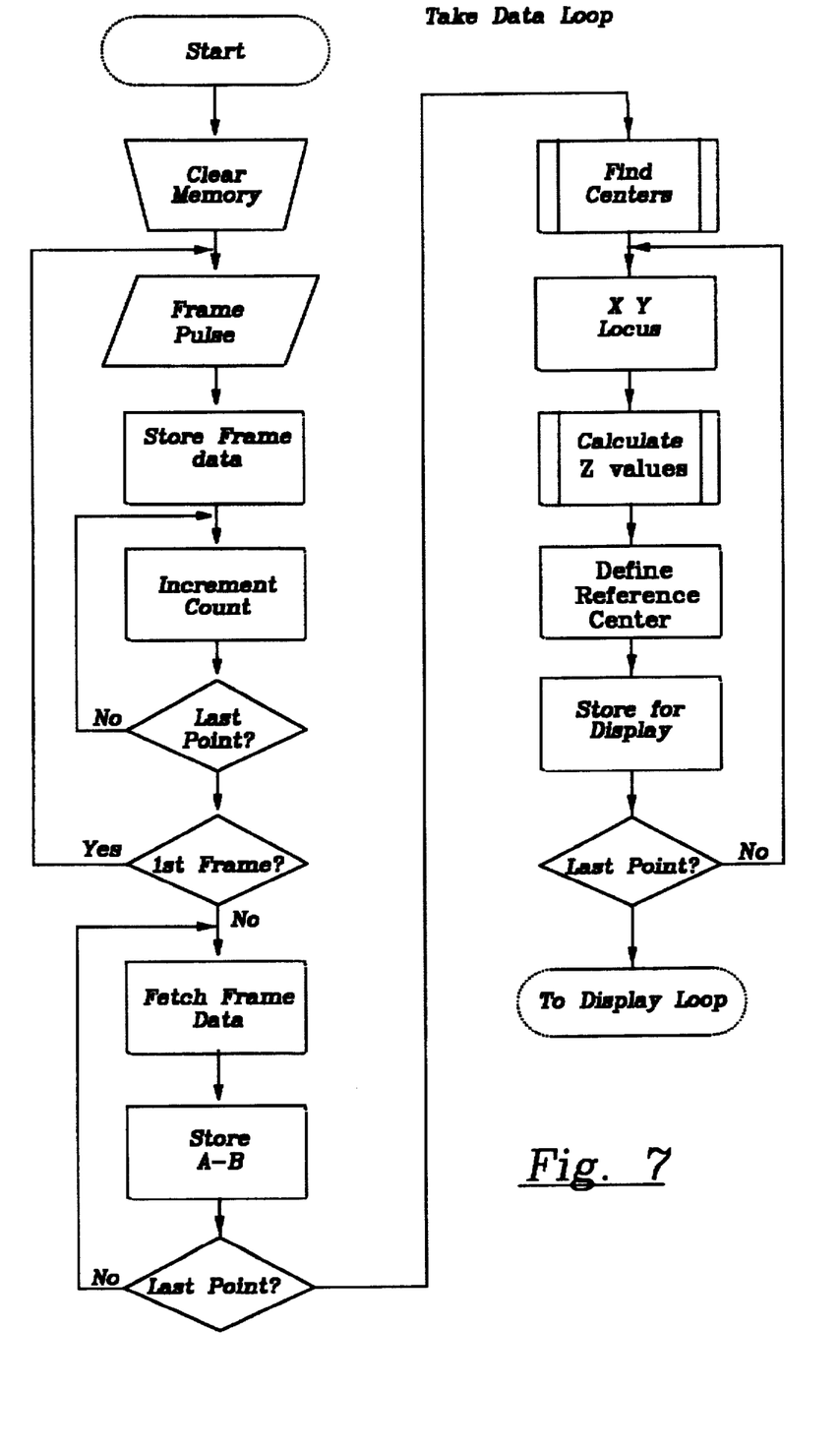
FIG. 7 is a program flowchart depicting a portion of the logical operation of the present invention.

Referring now to FIG. 7, which shows a sequence of operations employed in the present invention that is controlled by the associated computer. A portion of the program sequence is illustrated for explanation of a representative embodiment of the present invention.

The start of data acquisition is controllable in one of two ways: the sequence repeats for each video frame either automatically or upon initiation by the operator via a switch. The choice of mode is at the user's discretion.

For a single data acquisition sequence, two successive video image pairs are captured. The target matrix 3 illuminated for the second image time in the sequence. At the time when a vertical blanking pulse is accompanied by a first field identification pulse, the sequence is begun. The digital data sequence from the charge coupled devices 4 or the analog to digital converter 14 (via the multiplexer 34) represents the brightness of each of the sequential pixels that comprise the pictorial information. These data points are placed in sequential loci in the associated memory 18 (see FIG. 1) through the action of an address counter 19 that serves to define the storage location of each element received. The process continues until the last pixel of the current picture pair is captured. Then the target matrix illumination is turned on and the sequence is repeated thereby storing the second picture pair in additional memory pages.

After both sequential pictures have been captured and stored in this manner, the content of the areas of memory 18 that contain the first and second picture from each camera 4 are compared by subtraction on a pixel by pixel basis. In the event that no image of the reflection of a target matrix point 36 is encountered at the instant location, the numerical result of the subtraction will approximate zero. The value may not be exactly zero because each picture contains some degree of noise; however, the magnitude of the number so derived will be small compared to the alternative condition in which a target matrix reflection is encountered in the second exposure data from either camera 4. The data points with non-zero values, so defined, represent the reflected image of the target matrix 3 from the different camera angles. These points are stored in another portion of the memory 18 for further processing and ultimately for display.

In an alternative embodiment, only the pair of images containing the illuminated matrix image are defined for storage and analysis. In this configuration described above, the target matrix 3 is provided with an infra-red pass filter as are the camera lenses 10. In this embodiment, only the images of the matrix points 36 are imaged so the subtraction process is not required. The calculations are more complex, but the time required for image capture is reduced by one half. This configuration also eliminates the potentially distracting flash of light from the surgeon's view which is desirable in some instances. Both systems may be contained in a single instrument with the user selecting the operational mode by a suitable switch or other command input.

The stored data pairs are then treated in conventional software programs to extract the X, Y location of all image points. The most common of these programs uses a matrix technique for examining a group of adjacent loci to determine the exact center of each image point on a point-by-point basis. After the image points are so identified, the known size of the image (based on data from a calibration table data) is compared with the apparent location from the video data. Simple trigonometric calculations provide the spatial data from the raw X, Y data pairs. Comparison between the sequential calculation from the paired images provides a means for rejection of erroneous points caused by system or image noise. This sequence continues until all data points for each of the two camera sources 4 has been calculated. The surface shape, as defined from two known angles, are then combined to provide a smooth surface curvature map for display by conventional techniques.

The present invention advantageously employs two cameras 4 in determining the surface curvature map. A single camera surface measurement has limited ability in determining the location of the center or centroid of points formed on a side of the cornea which is furthest from the camera 4 and slopes away from the camera. Angles corresponding to rays that come close to being tangent with the surface of the eye 1 and that slope away from the camera 4 and the projector 108 pose a problem. In contrast, the dual camera system of the present invention, which provides two cameras 4 that are directed at different portions of the eye 1, provides broader coverage over the eye. The coverage of each camera 4 also advantageously overlaps each other at the central zone of the corner, thus, providing additional coverage for the most important region of the eye 1.

As described above, the images from the paired cameras are converted into digital form by a sampling system commonly called a frame grabber. The stored digital images are compared in the associated computer.

In an alternative embodiment, the television cameras 4 are so structured as to provide a digital representation of the video information as opposed to the common analog data output. The digital data take the form of byte wide serial transfer of brightness information.

The interface to the memory 18 is through the addressing and timing system comprising the computer interface 15, mode controller 16, and address counter 19 which is controlled by the video synchronizing signals. After the capture of the four picture sequence, the data representing the stereo image sequence is in the form of 16 bit words comprising 8 bit bytes from both cameras 4 in paired relationship. This permits the use of relatively slow memory devices that reduces the cost of fabrication.

The data storage format also simplifies the data processing steps in which the subtraction process compares numerical brightness values. The upper and lower byte at each location defines the video data from the pair of cameras 4 while the sequential data location for storage of the second pair of pictures differs from the first pair by the state of a single, high order, address bit. The computer program is simplified by this addressing method because the paired data for the sequential frames are at identical loci except for a flag bit that is used as the most significant address bit. The initial subtraction step for removing the background information is made by setting the flag bit and reading the data as the addend, and then resetting the flag bit and reading the data as the augend with the sign bit inverted. The resultant is then stored in memory 18 as the difference between the time sequenced picture pairs. The data, thus stored, is then compared on a bit-by-bit basis against a numerical threshold amplitude value. The logical result is stored in a matrix that represents the X Y coordinates of the reflection of the target matrix for trigonometric evaluation of surface shape.

Prior to processing the video information, the instantaneous amplitude of the signal is converted into digital amplitude information by conventional "flash" A/D conversion and the data stored in a conventional random access memory. In conjunction with this data retrieval and conversion system, and in time synchronism with it, is a lamp control circuit which causes the projector lamp 31 (which may be of the gas discharge type) to be turned on for alternate non-interlaced fields of the video. (In an alternative embodiment, which is not illustrated, the illumination sequence is derived by a mechanical shutter interposed in the projector illumination system 108.)

Since the target 3 is illuminated for one field and extinguished for the second, there is a difference between the two sequential video frames in that only one includes the pattern generated by the reflection from the corneal stroma of the target matrix 3. The second frame data, obtained while the lamp 31 is off, is digitized as was the first frame. At the same time, the memory contents that define the numerical representation of locus brightness from the first frame are extracted and numerically compared to the current value. A comparison between the first frame and the second frame is possible because the eye 1 is stationary and the time domain is controlled by a synchronizing signal source of high stability. It follows that the numerical difference between the two sequential points that describe the same spatial point will be very low in the areas of no target image and high in the areas of the image.

This subtraction will provide a new set of data points in numeric form for analysis that may be subjected to the edge detection means previously described to reduce the number of points to be analyzed. In practice, the two defined image points (less background clutter) from the cameras 4 may be averaged and compared with a preset value to determine which points are valid, and therefore, should be saved. It should be noted that the storage must involve both the magnitude and the screen locus in order for the computer analysis to define the shape of the reflections. If there is not good agreement of the X, Y, Z locus between the two camera definitions of a point's location, the point would be discarded. This electrical analog of the image from the corneal stroma forms the basis for the contour measurements to be performed.

As describe above, projector system 108 forms an image of the target matrix 3 on the eye 1. The target matrix 3 comprises a pattern of transparent points 36. The pattern of transparent points 36 that is to be obtained is determined by (1) the desired areas to be defined, (2) the resolution to be obtained in the spatial definition, and (3) the computer program size and speed available. The central zone, which is about 3 millimeters in diameter, contains the primary image forming section of the corneal "lens." This central zone is the most important area to adjust. Consequently, the measuring point 36 are closer together in this area. When the points are situated closer together, more calculations must be completed to define the centroids. Likewise, more computation is required to arrive at a smooth surface for display. However, the surgeon desires systems that provide data quickly and within a reasonable error range. Unfortunately, solving more calculations in a fixed time frame requires a system that is more powerful and, hence, more expensive.

The depth of focus of the projection system 108 for providing the matrix of points to be used for keratometric determination should be as high as possible to reduce defocusing with variation of lens 31 to eye 1 distance. An acceptable blur spot is related to the pixel pitch of the camera system 4. This spot size must be small enough that it will have no adverse effect on the image to be digitized.

The convergence angle of the beam is related to the focal distance to the object plane and the focal ratio of the lens 31. The aperture sine must remain small for the depth of focus to be adequate for the depth of the anterior chamber plus some extra amount to compensate for mis-positioning of the keratometric apparatus of the present invention. The actual calculations for these definitions are well known in the art and are not detailed here.

The use of simple lens projection coupled with the required small aperture causes an uneven illumination of the charge coupled device in the cameras 4. To compensate for the variation of video gain required for linearization of video response, a novel system is employed. The essentially parabolic loss curve from center is characterized on a pixel locus basis in numerical terms during calibration by the user. This numerical value is used to vary the numerical gain of an amplifier pair interposed between the charge coupled device and the usual processing chip.

The readout of the video signal from the charge coupled device chip 120 is an alternating process between two interleaved shift registers. The video level is transferred on alternating clock cycles from the parallel shift registers and combined by a time division multiplex scheme in the processing chip 122. See FIG. 8. The clock frequency component is removed by a low pass filter system which is also a part of the processing chip circuitry. In the scheme of the present invention, a current feedback amplifier pair 124 is connected to the charge coupled device video output lines 126. The feedback loop is constructed by a digital to analog conversion scheme where the connection between the amplifier output 128 and inverting input terminals 130 is a digital to analog converter 132 operating as a current controller driven by a parallel digital input 134 from a read only memory 136. The data contained in this ROM 136 is the pixel-by-pixel gain conversion factor for the linearization/compensation. As a result of the alternating nature of the data stream, the settling time for each amplifier 124 is increased.

Taking the standard NTSC television raster with an assumed 640 pixels per line the following calculations can be made. The horizontal rate of 15,750 lines per second, which equals 63.5 microseconds per line, minus the blanking period of 11.3 microseconds yields 52.2 microseconds of active video per line. Then, given 640 pixels per line, each pixel is $52.2/640$ or 82 nanoseconds per pixel. Since there are two alternating data streams with 50% duty cycles, the clock period would be 163 nanoseconds for each full cycle with a dual phase clocking scheme.

Figure 8:
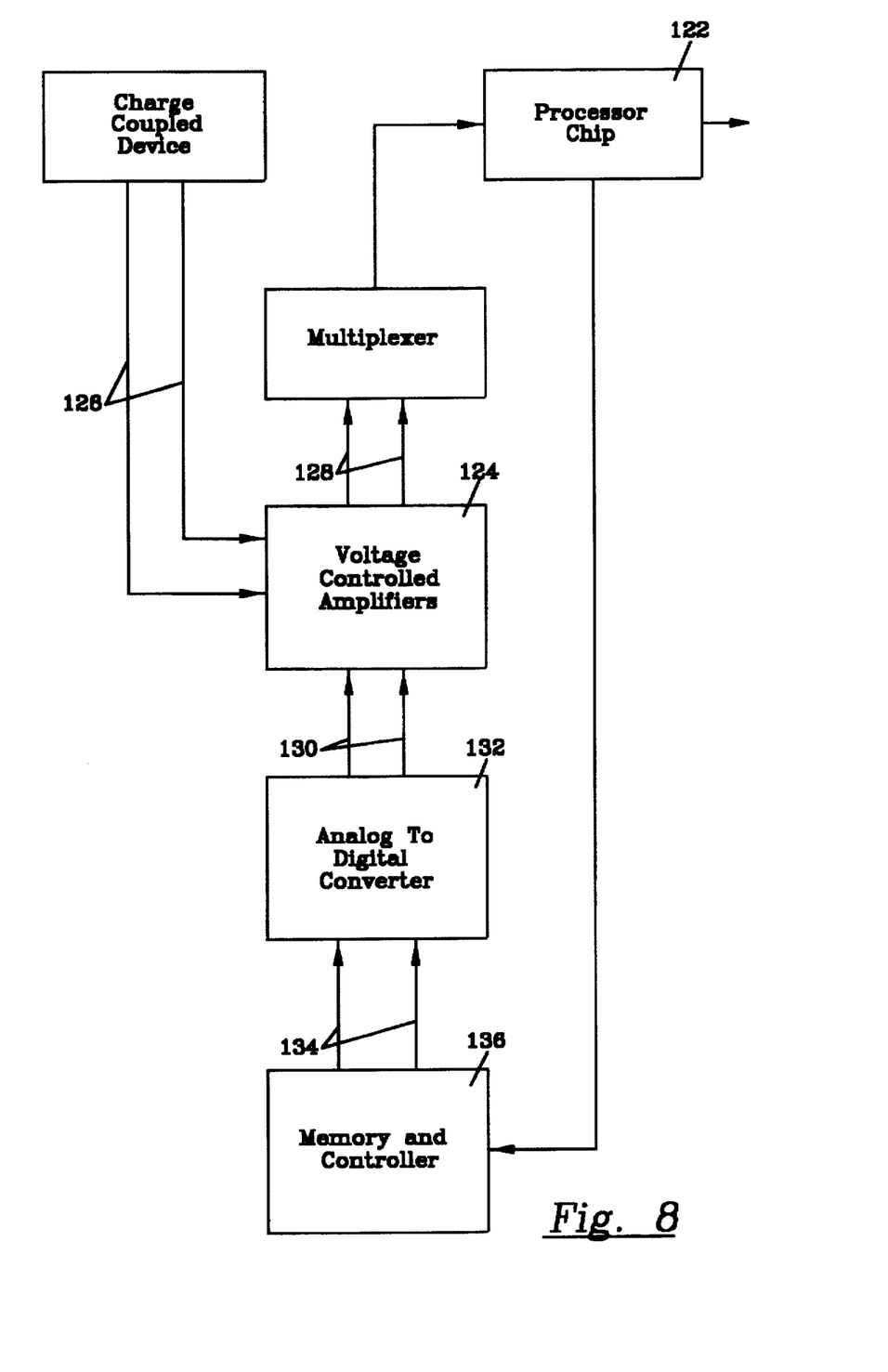
FIG. 8 is a block diagram depicting the camera video processing system employed for normalization of effective elemental brightness of the corneal image.

On the logical low, the A/D converter 152 sets the amplifier gain as the shift register clocks out the video data. The logic high condition is then sampled by the time division multiplexer as the instantaneous video analog level is modified by the A/D conversion control of gain. The clock signal is available from the video processor chip in the camera 4. The dual phase conversion is accomplished by using a simple inverter scheme and the remainder of the camera operation is not affected. These numerical details are representative of a common video and camera combination which would require recalculation for cameras 4 with different timing or pixel pitch characteristics as will be obvious to one skilled in the art.

In the event that the Automatic Light Compensation/Automatic Gain Compensation circuits are not to be used, the multiplexing and filtering is done in an external processor. This permits the use of fixed gain and, consequently, provides photometric data not commonly available from inexpensive cameras because the compensation signals change the amplitude response of the charge coupled device and it's output after processing. The availability of high quality charge coupled device chips from several vendors makes this scheme the desired one. The sampled picture system with a strobe lamp slaved to the video reset and data storage initiation are the keys to this enhanced but simpler camera system. The analog sampling in the A/D converter can be made twelve rather than the common eight bits to encompass the greater dynamic range anticipated without loss of data.

With the apparatus of the present invention, capture of the paired images is preferably by paired analog to digital converters but in an alternative construction, the data streams are time division multiplexed to a single analog to digital converter. The advantage lies in the common amplifier and reference which reduces errors, but the single converter system requires much faster memory and amplifier components which increases production costs.

As described above, the cameras 4 may comprise charge coupled devices. However, other suitable detectors 4 may also be employed in the practice of the invention. Examples of other detectors 4 suitably employed in the apparatus and method of the present invention include vidicons and similar vacuum tube pickups.

The most common integrated circuit charge coupled device camera photosensitive matrix is about one-third inch (approximately 9 millimeters) in diagonal measure. The typical limbus of the normal human eye is on the order of about 12 millimeters in diameter. The camera must provide an image of this entire area for analysis. The desired image is on the order of about three millimeters in diameter (or somewhat less) to allow all of cornea to the limbus, with the target matrix reflection to be seen in all cases. The size of this image is chosen to meet the previous limitation so that the outer reflection will be visible in the television picture with a minimum of extra coverage. The vertical size of the picture is less than the horizontal by a ratio of 3:4 (FIG. 5). The desired image must fill ¾ of the charge coupled device faceplate, or somewhat more, allowing for the normal overscan and the fact that the image must fit within the picture area irrespective of the limbal diameter. Consequently, the image of the target reflection will be on the order of about three millimeters in diameter.

From these specifications and the focal distance of the microscope 100, the camera lens focal length may be calculated. For example, a Zeiss OPMI-6 microscope fitted with a 180 mm focal length objective lens would require a camera lens focal length of about 36 mm. The magnification ratio of 12:3 (4:1) and the required lens to eye 1 distance are calculated from the given relationships. As is well known, the sum of the reciprocals of the image and object distances provides the reciprocal of the lens focal length. In similar fashion, the faceplate image magnification ratio at the camera may be derived for microscope objective lens focal length.

With this magnification ratio known, the effective aperture can be determined. This permits the estimation of the faceplate illumination to be available for any given target matrix illumination level.

Figure 9:
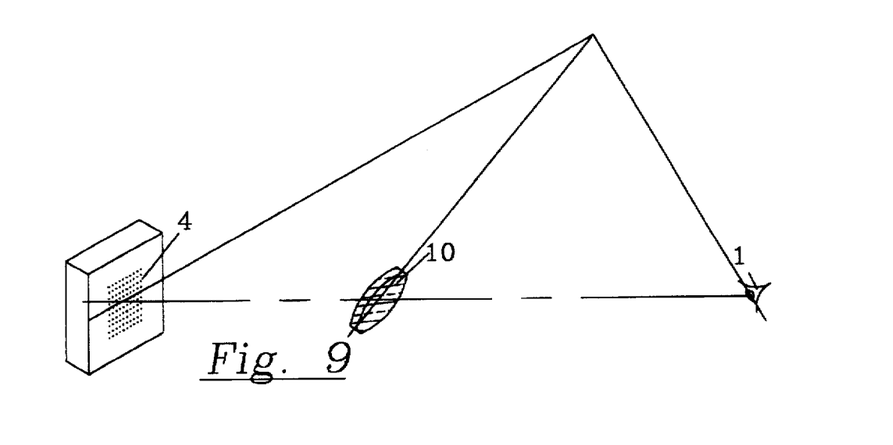
FIG. 9 is a perspective view depicting the Scheimpflug construction of the present invention.

FIG. 9 shows an arrangement between the detector 4, the camera lens 10, and the eye 1 being examined as employed in the present invention. As shown in FIG. 9, the image and object planes are not both parallel and perpendicular to the optical axis 112 of lens 10.

Optical image degradation occurs when the image and object planes are not both parallel and perpendicular to the optical axis 102 of the projection lens 32. In ophthalmic photography, and for keratometry in particular, the object plane is inclined to the optical axis and the conjugate ratio is on the order of 1:2. Accordingly, the lens and focal planes must be rotated to provide best overall image sharpness. The Scheimpflug principle is used to accomplish this task. Specifically, the Scheimpflug principle is employed for depth of field improvement. The reduction of geometric distortion in photographs by the Scheimpflug rule or law is well known to commercial photographers, and the application of this principle in keratometry is contained in my previous patent, U.S. Pat. No. 5,512,966. When an object at a near point is not parallel to the focal plane of the camera, a photograph will demonstrate the distortion where parallel planes of the object seem to converge in the photograph. In addition, the depth of focus is often inadequate to render sharply all portions of the object to be photographed.

The small subject distance involved in ophthalmic photography by a conventional slit lamp camera exaggerates this pictorial distortion. The angle of the optical axis of the microscope to the optical axis of the camera places the image in a plane which is not perpendicular to the optical axis of the camera. In addition, the design of the camera system which uses the bio-microscope for image sourcing imposes a severe limit on the faceplate illumination of the camera. At common magnifications, the system if on the order of f16, requires that large flash energy levels be employed for adequate exposure with high resolution color film.

In the present invention, orientation of the cameras 4 are adjusted to improve the depth of field.

The distortion introduced into the photographic image is related directly to the angular relationship employed. To compensate for the stretching of the image, the individual television raster line is compensated by application of simple geometry. The photographic image, as projected in a Scheimpflug rule focus compensated system, is in a plane that is at a defined angle to the optical axis 112 of the lens 10. FIG. 9 depicts this Scheimpflug rule focus compensated system.

The process used to compensate for the stretching of the image requires that the image be compressed in the horizontal axis, which effectively increases the number of pixels per linear segment. Calculation of the X, Y loci before the compression to remove the Scheimpflug induced distortion provides the greatest accuracy in the shape determination because the number of pixels for a given surface area is increased over the undistorted values after compensation. This process is performed in instrument calibration by careful analysis of the images on flat planes at several known distances from the projector lens. A matrix or mathematical correction system constructed from these data serves to provide the geometrical correction for the construction of an accurate topographical map representation of the corneal surface area to be measured. The recalculation of the image to remove the distortion requires that this interpolation be performed to provide a smooth display of the surface geometry profile.

To further minimize the optical image degradation that occurs when the image and object planes are not both parallel and perpendicular to the optical axis 102 of the projection lens 32, the lens aperture must be at or near minimum for best depth of focus; this solution requires high light levels, which could cause retinal heating. To provide the required light without high average energy levels at the cornea, a short high intensity flash illumination source is employed (as described above) to reduce the energy entering the eye for safety reasons.

With regard to resolution, it will be appreciated that the resolution figures quoted by the builders of television cameras are not a true indication of the resolution obtainable with the present invention because these resolution figures are derived from modulation transfer functions that contain limitations imposed by the expected use. In the application of the present invention, the spatial frequency of the target matrix 3 is predictable and the effective system resolution can be made higher than the limit predicted by the manufacturer's specification sheets.

Additionally, the resolution of the data stored in the present invention is not a function of the memory size of the host system and, thus, permits the definition of the image to a much higher resolution limit than would be possible with direct digitization of the image and conventional image analysis algorithms as are used in the prior art. After the data are stored, a signal from the external computer (via the interface link 15) initiates the serial dump of the memory contents. This serial dump is conducted via the interface under control of the mode control 16, the clock generator (not shown), and the address counter 19. (It will be appreciated that the computer may be a part of the instrument so that no such data transfer would then be required.)

The technique employed by the present invention results in a substantial reduction of the number of data points that must be treated in the computer while retaining a degree of data redundancy that permits the system to reject noise contaminated data points by conventional signal averaging. This processing substitutes for the conventional software system and, the computations are simple and quick. Based upon this redundancy in the data to assure the accuracy of the measurement, there is no requirement for a large and complex computer and program system to derive the desired curvature values and the simple calculations are quickly performed.

Each target reflection produces one data point at each reflection edge point that is identified on the anterior corneal surface and, therefore, corneal surface shape. Further, the numerical scatter of the data points is a function of the focus and overall image quality. Accordingly, each measurement can be evaluated for minimum acceptable quality. A decision can then be made whether to reject any measurement that does not fulfill the quality standard set into the software.

When an image set has been stored by the previously detailed technique and the requisite computations performed in the computer, the digital information for defining the corneal shape can be displayed in some arbitrary color upon the unmodified image from the camera by conventional video mixer means. Alternatively, the data may be presented for use in any of several formats that are well known in the art.

Several computer generated data display formats are made available. These range from a numerical axis and magnitude in the eyepiece to computer CRT monitor displays such as a vector map with a line showing both axis and magnitude. The display may be with or without a series of concentric circles representing cylinder magnitude to give rapid assessment of astigmatism and to permit the surgeon to select a value that will result in the least residual astigmatism after healing is complete.

The user is most often interested in data presentation in terms of diopters variation from true symmetry of the cornea, and the conversion of the topographic data into dioptric form is trivial. Display of the derived data may be in graph form for ease of assimilation and application by the user. This is by means of conventional display algorithms and techniques that are machine dependent and will not be discussed in detail.

In an alternative embodiment, not illustrated, the monitor 12 and associated elements are not employed. Instead of the view of the monitor through the microscope eyepieces, the monitor 12 is a conventional computer display monitor mounted within the view of the surgeon if he raises his eyes from the microscope 100. The remote monitor system is less expensive but not as easily operated. Additionally, the surgeon must look away from the eye images. Consequently, there is some possibility for error in this alternative embodiment.

Thus, it can be seen that this system substitutes novel means and method for the conventional image analysis technique to permit the construction of a very inexpensive system that can be used to produce clinically useful data. In particular, the present invention uses a unique system of video image analysis to provide to the user full topographical mapping of the cornea. Almost instant display of the corneal radius at enough points to permit accurate assessment of the surface shape is provided. The use of a dual imaging system for providing accurate stereopsis and consequent surface mapping in the present invention is a significant improvement over the presently available techniques. The surgical keratometer system of the present invention is designed to eliminate most of the instrument related problems and to address the operational limitations in such a way as to provide the greatest safety and accuracy possible.

Additionally, the present invention eliminates the controls that must be manipulated by the surgeon and improves the accuracy and speed that are requisite for use with surgical lasers.

In particular, the present invention does not require manipulation of knobs or levers by the user and has no moving parts, consequently, eliminating the risk of contamination of the sterile field and making the use of the system as simple as possible. Illumination of the target matrix lamp(s) 31 is controlled by either a foot pedal or a push button, operable by the nurse, to free the surgeon from distracting lights in the field of view except when the system is in use. In an alternative construction described above, the illumination is confined to a narrow band in the near infra-red and the apparatus makes automatic measurements at predetermined temporal intervals.

Prior art systems use only a single tangent slope calculation that can be in error due to (1) improper focal distance without the user being aware of the error and (2) the invalid assumption of an axial radius of curvature such as would be produced by spherical surfaces. In contrast, the present invention provides a system of cross checking to ensure the accuracy of the corneal shape data. The system of the present invention also reduces the effect of lens to object distance that might result from inaccurate focusing by the operator; see above-mentioned U.S. Pat. No. 5,512,965.

The surgical keratometer of the present invention makes use of a microcomputer to provide fast and accurate measurements without the limitations of the other available systems. With careful use, the system will consistently provide information to the surgeon to quantify the surface shape as the therapeutic procedure is being conducted so that the surgeon may better judge the results.

Thus, there has been disclosed a method and apparatus for measuring surface topography of a cornea. The method and apparatus of the invention for measuring surface topography of a cornea can be applied to surgical procedures and, in particular, to corneal surgery. The foregoing descriptions of one embodiment of the present invention is representative of the techniques employed and these descriptions are not intended as a limit on the scope of the invention. It will be readily apparent to those skilled in this art that various changes and modifications of an obvious nature may be made, and all such changes and modifications are considered to fall within the scope of the invention, as defined by the appended claims.

What is claimed is:

1. An instrument for measuring surface topography of a cornea during surgery, said instrument comprising:

(a) an optical projector that projects a pattern onto said cornea, said pattern comprising a plurality of isolated points;

(b) a first camera and a second camera each comprising a camera lens and a detector array, said first camera, said second camera, and said projector directed toward a single point, said first camera and said second camera producing images of said plurality of isolated points projected on said cornea, said location of each of said isolated points on said cornea dependent upon said surface topography;

(c) a computer processor that employs triangulation calculations to determine said surface topography from said location of said isolated points on said cornea; and (d) a display for displaying said surface topography.

2. The instrument of claim 1 further comprising a first filter having a first transmission band in the infrared region placed between said cornea and a light source, and a second filter having a second transmission band in the infrared region placed between said cornea and each said detector array, said first and said second transmission bands overlapping.

3. The instrument of claim 1 wherein said projector comprises a light source, a projection lens, and a target therebetween, said target having said plurality of isolated points formed therein, said light source illuminating said target and said projection lens.

4. The instrument of claim 1 wherein said optical projector, said first camera, and said second camera are attached to a microscope having at least one eyepiece.

5. The instrument of claim 4 wherein said microscope includes at least one eyepiece and said display is visible through said eyepiece.

6. The instrument of claim 1 wherein said detector array is selected from the group consisting of a charge coupled device array, a vidicon, and a vacuum tube pickup element.

7. The instrument of claim 1 wherein said display provides a contour map of the surface of said cornea.

8. An instrument for measuring surface topography of a cornea, said instrument comprising:
   (a) an optical projector that projects a pattern onto said cornea, said optical projector having an optical axis, said pattern comprising a plurality of isolated points;
   (b) a first camera and a second camera each comprising a camera lens and a detector array, each said camera having an optical axis, said optical axis of each of said first camera, said second camera, and said projector intersecting at a single point, said first camera and said second camera producing images of said plurality of isolated points projected on said cornea, said location of each of said isolated points on said cornea dependent upon said surface topography;
   (c) a computer processor that employs triangulation calculations to determine said surface topography from said location of said isolated points on said cornea; and
   (d) a display for displaying said surface topography.

9. The instrument of claim 8 wherein said projector comprises a light source, a projection lens, and a target therebetween, said target having said plurality of isolated points formed therein, said light source illuminating said target and said projection lens, said optical axis of said projector corresponding to said optical axis of said projection lens.

10. A method of measuring surface topography on a cornea during surgery, said method comprising the steps of:
    (a) projecting a pattern onto said cornea using a projector, said pattern comprising a plurality of discrete points, said location of each of said discrete points on said cornea dependent upon said surface topography;
    (b) directing a first camera, a second camera, and said projector toward a single point in space, each said cameras comprising a camera lens and a detector array;
    (c) placing said cornea at a position between said single point in space and said first camera, said second camera, and said projector;
    (d) obtaining images of said discrete points projected on said cornea with said first camera and said second camera;
    (e) employing triangulation calculations to determine said surface topography from said location of said discrete points on said cornea; and
    (f) displaying said surface topography.

11. The method of claim 10 wherein said first camera and said second camera obtain a first pair of images of said cornea during a first interval when said pattern is projected on said cornea and a second pair of images during a second interval when said pattern is not projected on said cornea, and wherein said a second pair of images obtained during said second interval are subtracted from said images obtained during said first interval, thereby removing background clutter.

12. The method of claim 10 further comprising placing a first filter having a first transmission band in the infrared region between a cornea and a light source, and a second filter having a second transmission band in the infrared region between said cornea and each said detector array, said first and said second transmission bands overlapping.

13. The method of claim 10 wherein said projector comprises a light source, a projection lens, and a target therebetween, said target having said plurality of discrete points formed therein, said light source illuminating said target and said projection lens.

14. The method of claim 10 further comprising attaching said projector, said first camera, and said second camera, to a microscope.

15. The method of claim 14 wherein said microscope includes at least one eyepiece and said display is visible through said eyepiece.

16. The method of claim 10 wherein said detector array is selected from the group consisting of a charge coupled device array, a vidicon, and a vacuum tube pickup element.

17. The method of claim 10 wherein said topography is measured during corneal surgery.

18. The method of claim 10 wherein said images of discrete points projected on said cornea are simultaneously obtained with said first camera and said second camera.

* * * * *